United States Patent
Erkens et al.

(10) Patent No.: US 10,918,890 B2
(45) Date of Patent: Feb. 16, 2021

(54) BLEACHING AGENTS HAVING REDUCED OIL-SEPARATION TENDENCY

(71) Applicant: Henkel AG & Co. KGaA, Duesseldorf (DE)

(72) Inventors: Udo Erkens, Willich (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 254 days.

(21) Appl. No.: 15/547,066

(22) PCT Filed: Oct. 30, 2015

(86) PCT No.: PCT/EP2015/075202
§ 371 (c)(1),
(2) Date: Jul. 28, 2017

(87) PCT Pub. No.: WO2016/124265
PCT Pub. Date: Aug. 11, 2016

(65) Prior Publication Data
US 2018/0001117 A1     Jan. 4, 2018

(30) Foreign Application Priority Data
Feb. 6, 2015  (DE) ........................ 10 2015 202 188

(51) Int. Cl.
| | | |
|---|---|---|
| *A61Q 5/00* | (2006.01) | |
| *A61Q 5/08* | (2006.01) | |
| *A61K 8/81* | (2006.01) | |
| *A61K 8/23* | (2006.01) | |
| *A61K 8/31* | (2006.01) | |
| *A61K 8/92* | (2006.01) | |

(52) U.S. Cl.
CPC .................. *A61Q 5/08* (2013.01); *A61K 8/23* (2013.01); *A61K 8/31* (2013.01); *A61K 8/8111* (2013.01); *A61K 8/92* (2013.01); *A61K 2800/48* (2013.01)

(58) Field of Classification Search
CPC .......... A61Q 5/08; A61K 8/31; A61K 8/8111; A61K 8/23; A61K 8/92; A61K 2800/48; A61K 8/22; A61K 2800/882; A61K 8/46; A61K 2800/31
USPC .......................................................... 424/62
See application file for complete search history.

(56) References Cited

U.S. PATENT DOCUMENTS

| | | | |
|---|---|---|---|
| 6,365,136 B1 | 4/2002 | Lauscher et al. | |
| 8,133,285 B2 | 3/2012 | Jordan et al. | |
| 2009/0202598 A1* | 8/2009 | Kravtchenko | A61K 8/068 424/401 |
| 2013/0266529 A1* | 10/2013 | Deconinck | A61K 8/365 424/62 |

FOREIGN PATENT DOCUMENTS

| | | | | |
|---|---|---|---|---|
| EP | 1034777 A1 * | 9/2000 | ............ | A61K 8/135 |
| WO | 2009134875 A2 | 11/2009 | | |

OTHER PUBLICATIONS

STIC Search Report dated Sep. 25, 2018.*
English translation (Sep. 26, 2018) of the EP Patent No. 1034777 A1.*
EPO, International Search Report and Written Opinion issued in International Application No. PCT/EP2015075202, dated Dec. 23, 2015.

* cited by examiner

Primary Examiner — Eisa B Elhilo
(74) Attorney, Agent, or Firm — Lorenz & Kopf, LLP

(57) ABSTRACT

Bleaching agents with improved resistance to oil separation and better miscibility with dye-containing formulations comprise—in relation to their weight—from about 0.015 to about 10 wt.-% ethylene octene copolymer(s), from about 5 to about 70 wt.-% oil component(s), from about 1 to about 70 wt.-% peroxydisulfate(s) chosen from the group of sodium peroxodisulfate and/or potassium peroxodisulfate and/or ammonium peroxodisulfate, and ≥1 wt.-% free water.

19 Claims, No Drawings

BLEACHING AGENTS HAVING REDUCED OIL-SEPARATION TENDENCY

CROSS-REFERENCE TO RELATED APPLICATION

This application is a U.S. National-Stage entry under 35 U.S.C. § 371 based on International Application No. PCT/EP2015/075202, filed Oct. 30, 2015 which was published under PCT Article 21(2) and which claims priority to German Application No. 10 2015 202 188.2, filed Feb. 6, 2015, which are all hereby incorporated in their entirety by reference.

TECHNICAL FIELD

The present disclosure relates to agents for oxidative color changes in the field of cosmetics which are particularly suitable for lightening keratin fibers, in particular human hair.

BACKGROUND

The oxidizing agents contained in bleaching agents are able to lighten hair fibers by the oxidative destruction of the hair dye melanin. For a moderate bleaching effect, the use of hydrogen peroxide, if necessary using ammonia or other alkalizing agents, is sufficient as an oxidizing agent alone, and a mixture of hydrogen peroxide and peroxo disulfate salts and/or peroxomonosulfate salts is usually used for achieving a stronger bleaching effect.

For reasons of stability, commercially available bleaching agents are usually offered in two separately packaged preparations which are mixed into a ready-to-use form immediately before application. Usually, commercially available bleaching agents include a liquid oxidizing agent preparation and a powder which contains solid oxidizing agents. Alternatively, instead of the powder, paste-like agents can be mixed with a liquid oxidizing agent preparation, by which the problem of dusting during preparation and mixing is avoided. Products having additional components are also offered in the trade.

Paste-like bleaching agents usually contain larger quantities of an inert oil, which can lead to stability problems (settling of the solid oxidizing agents from the oil and deposition of the oil component). Even if the peroxydisulfates are not yet completely settled, a concentration gradient can occur within the packaging, so that different portions of the packaging can cause different lightening after the mixing. A high viscosity is desirable to minimize these problems.

On the other hand, the viscosity of the bleaching paste must be so low that it can be mixed well and quickly with the liquid oxidizing agent preparation. In the case of water-free bleaching agents, easy and homogeneous miscibility with the mostly aqueous oxidizing agent preparation is a particularly important and technically complex requirement.

The resulting bleaching mixture must also be liquid enough to allow itself to be applied easily and uniformly, but thick enough to not drip off the head or application aids such as brushes. In addition, the resulting bleaching mixture should not separate, as sedimentation or phase separation is perceived by the customer as a quality deficiency.

Often, hair is not only being lightened but colored at the same time. Bleaching pastes should therefore also be readily miscible with creamy dyes. Often, these coloring agents contain direct-acting dyes, so that homogeneous mixing is a prerequisite for a uniform dyeing and lightening result.

WO 2009/134875 A1 describes bleaching agents which contain persulfate salts and an oil gel, which in turn is composed of oil(s) and certain polymers.

EP 1 034 777 A1 discloses an agent for lightening keratin fibers which contain at least two preparations (A) and (B) packaged separately from each other which are mixed immediately before application into an application mixture, wherein the preparations (A) are oil-based and contain polymer(s) which form oleo and/or lipogels. Mixtures with natural polymers, for example xanthan, are also disclosed.

BRIEF SUMMARY

Agents for lightening keratin fibers and methods for the color change of keratin fibers are provided herein. In an embodiment, an agent for lightening keratin fibers includes—based on its weight—a) from about 0.015 to about 10% by weight of ethylene-octene copolymer(s), b) from about 5 to about 70% by weight of oil component(s), c) from about 1 to about 70% by weight of peroxodisulfate(s) chosen from the group of sodium peroxodisulfate and/or potassium peroxodisulfate and/or ammonium peroxodisulfate, d) ≤about 1% by weight free water.

In another embodiment, a method for the color change of keratin fibers is provided. In accordance with the method, at least two preparations (A) and (B) are packaged separately from each other, of which preparation (A) comprises at least one persulphate and preparation (B) comprises at least one oxidizing agent. The preparations (A) and (B) are mixed to form an application mixture. The application mixture is applied to the fibers and is rinsed off again after an exposure time. Preparation (A) comprises a) from about 0.015 to about 10% by weight of ethylene-octene copolymer(s), b) from about 5 to about 70% by weight of oil component(s), c) from about 1 to about 70% by weight of peroxodisulfate(s) chosen from the group of sodium peroxodisulfate and/or potassium peroxodisulfate, d) ≤about 1% by weight of free water.

In another embodiment, an agent for lightening keratin fibers is provided. The agent includes—based on its weight, a) from about 0.4 to about 3% by weight of ethylene-octene copolymer(s), b) from about 32.5 to about 50% by weight, of oil(s) chosen from the group of paraffin oil, polyisobutene, the alkylbenzoates, isopropyl palmitate, the $C_{14-22}$-alkanes, isononyl isononanoate, or combinations thereof, c) from about 12.5 to about 45% by weight of peroxodisulfate(s) chosen from the group of sodium peroxodisulfate and/or potassium peroxydisulfate, d) ≤about 1% by weight free water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It was an object of the present disclosure to further improve the properties of bleaching agents, by increasing the stability against oil separation. Moreover, the miscibility with dye-containing formulations should be improved.

It has been shown that the use of certain copolymers solves the above-mentioned problems in anhydrous systems.

Desirable properties of the agent according to the present disclosure are stability against settling and phase separation.

The object of the present disclosure is, in a first embodiment, an agent for lightening keratin fibers, containing—based on their weight a) from about 0.015 to about 10% by weight of ethylene-octene copolymer(s),
b) from about 5 to about 70% by weight of oil component(s),
c) from about 1 to about 70% by weight of peroxodisulfate(s) chosen from the group of sodium peroxodisulfate and/or potassium peroxodisulfate and/or ammonium peroxodisulfate,
d) ≤about 1% by weight free water.

Keratinic fibers or also keratin fibers are understood to mean furs, wool, feathers and, in particular, human hair. Although the agents as contemplated herein are primarily suitable for lightening keratin fibers, there is nothing in principle opposed to use in other fields.

The compositions as contemplated herein contain a maximum of about 1% by weight, preferably a maximum of about 0.5%, of free water. For the purposes of the present application, "free water" is water which is not contained in the form of water of crystallization, water of hydration or similar molecularly bound water in the composition. The content of water of crystallization, water of hydration or similar molecularly bound water, which is contained in the components used, does not constitute free water in the sense of the present application. Free water is, for example, such water which is added to the composition as contemplated herein as a solvent, as a gel activator or as a solvent component of other active ingredients.

As a first ingredient, the agents as contemplated herein contain one or more copolymer(s) of ethylene and octene. Preferred copolymers are those of ethylene and 1-octene. The monomer units of the copolymers can be present distributed over the polymer molecule, but preference is given, as contemplated herein, for the use of block copolymers which have (possibly multiple) blocks of multiple ethylene units and multiple octene units.

Particularly preferred agents as contemplated herein are exemplified in that they contain block copolymers of ethylene and octene, which contain structural units of the formulas (I) and (II):

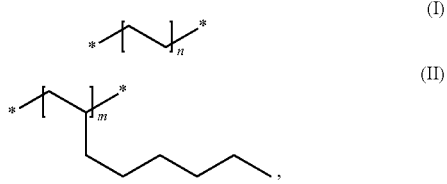

in which n and m, independently of one another, are integers from 10 to about 500.

The copolymer(s) of ethylene and octene used as contemplated herein may contain further monomers, wherein preferred agents as contemplated herein are exemplified in that they contain copolymers of ethylene and octene which are configured of at least about 50 mole %, preferably at least about 60 mole %, more preferably at least about 70 mole %, especially preferably at least about 80 mole %, and in particular at least about 90 mole %, of ethylene and octene.

Extremely preferred agents contain copolymer(s) of ethylene and octene, which contain no further monomer units apart from ethylene and octene units.

Irrespective of which copolymer(s) of ethylene and octene are used in the agents as contemplated herein, agents which contain from about 0.05 to about 7.5% by weight of ethylene-octene copolymer(s) are preferred, more preferably from about 0.1 to about 6% by weight, further preferably from about 0.15 to about 5% by weight, particularly preferably from about 0.2 to about 4% by weight, and in particular from about 0.4 to about 3% by weight.

The copolymer(s) of ethylene and octene, in combination with the ingredients b) and c), lead to comfortable viscous bleaching pastes which exhibit excellent stability with drastically reduced oil separation. In addition, the miscibility with dye-containing formulations and with the developer emulsion is markedly improved. The ready-mixed bleaching agents also show a very suitable and stable viscosity for the application area.

As a second ingredient, the agents as contemplated herein contain from about 5 to about 70% by weight of oil component(s). Preferably, this/these oil(s) is/are liquid at 25° C.

In the case of cosmetic oils, volatile and non-volatile oils are distinguished from each other. Non-volatile oils are understood to mean those oils which have a vapor pressure of less than 2.66 Pa (0.02 mm Hg) at 20° C. and an ambient pressure of 1013 hPa. Volatile oils are understood to mean those oils which have a vapor pressure of from about 2.66 Pa–about 40000 Pa (from about 0.02 mm–about 300 mm Hg) at 20° C. and an ambient pressure of 1013 hPa, preferably from about 10–about 12,000 Pa (from about 0.1–about 90 mm Hg), particularly preferably from about 13–about 3000 Pa, most preferably from about 15–about 500 Pa.

Volatile cosmetic oils are usually selected from cyclic silicone oils having the INCI name cyclomethicone. The INCI name cyclomethicones is understood to mean in particular cyclotrisiloxane (hexamethylcyclotrisiloxane), cyclotetrasiloxane (octamethylcyclotetrasiloxane), cyclopentasiloxane (decamethylcyclopentasiloxane) and cyclohexasiloxane (dodecamethylcyclohexa siloxane). These oils have a vapor pressure of from about 13–about 15 Pa at 20° C.

A preferred cyclomethicone substitute as contemplated herein is a mixture of $C_{13}$-$C_{16}$ isoparaffins, $C_{12}$-$C_{14}$ isoparaffins and $C_{13}$-$C_{15}$ alkanes whose viscosity at 25° C. is in the range from about 2 to about 6 mPas and which has a vapor pressure at 20° C. in the range of from about 10 to about 150 Pa, preferably from about 100 to about 150 Pa. Such a mixture is, for example, available under the name SiClone SR-5 from Presperse Inc.

Further preferred volatile silicone oils are selected from volatile linear silicone oils, in particular volatile linear silicone oils having 2 to 10 siloxane units, such as hexamethyldisiloxane (L2), octamethyltrisiloxane (L3), decamethyltetrasiloxane (L4), as are available, for example, in the commercial products DC 2-1184, Dow Corning® 200 (0.65 cSt) and Dow Corning® 200 (1.5 cSt), and low molecular weight phenyl trimethicones having a vapor pressure at 20° C. of about 2000 Pa, as is available, for example, from GE Bayer Silicones/Momentive under the name Baysilone Fluid PD 5.

Further preferred products as contemplated herein contain at least one volatile non-silicone oil. Preferred volatile non-silicone oils are selected from $C_8$-$C_{16}$ isoparaffins, in particular from isononane, isodecane, isoundecane, isododecane, isotridecane, isotetradecane, isopentadecane and isohexadecane, and mixtures thereof. $C_{10}$-$C_{13}$-isoparaffin mixtures, in particular those having a vapor pressure at 20° C. of from about 10-about 400 Pa, preferably from about 13-about 100 Pa, are preferred.

Further especially preferred cosmetic oils as contemplated herein are esters of linear or branched saturated or unsaturated fatty alcohols having 2 to 30 carbon atoms with linear or branched saturated or unsaturated fatty acids having 2 to 30 carbon atoms which may be hydroxylated. Preference is given to esters of linear or branched saturated fatty alcohols having 2 to 5 carbon atoms with linear or branched saturated or unsaturated fatty acids having 10 to 18 carbon atoms which may be hydroxylated. Preferred examples thereof are isopropyl palmitate, isopropyl stearate, isopropyl myristate, 2-hexyldecyl stearate, 2-hexyldecyl laurate, isodecyl neopentanoate, isononyl isononanoate, 2-ethylhexyl palmitate and 2-ethylhexyl stearate. Also preferable are isopropyl isostearate, isopropyl oleate, isooctylstearate, isononyl stearate, isocetyl stearate, isononyl isononanoate, isotridecyl isononanoate, cetearyl isononanoate, 2-ethylhexyllaurate, 2-ethylhexyl isostearates, 2-ethylhexyl cocoate, 2-octyldodecyl palmitate, butyl octanoic acid 2-butyloctanol, diisotridecylacetate, n-butyl stearate, n-hexyl laurate, n-decyl oleate, oleyl oleate, oleyl erucate, erucyl oleate, erucyl erucate, ethylene glycol diolate, ethylene glycol dipalmitate, n-hexyl laurate, n-decyl oleate, oleyl oleate, oleyl erucate, erucyl oleate, $C_{12}$-$C_{15}$ alkyl lactate and di-$C_{12}$-$C_{13}$-alkyl malate and the benzoic acid esters of linear or branched $C_{8-22}$-alkanols. Particular preference is given to benzoic acid $C_{12}$-$C_{15}$-alkyl esters, e.g., commercially available as Finsolv® TN ($C_{12}$-$C_{15}$-alkylbenzoate), and benzoic acid isostearyl esters, e.g., available as Finsolv® SB, 2-ethylhexylbenzoate, e.g., available as Finsolv® EB, and benzoic acid 2-octyldodecyl esters, for example, available as Finsolv(r) BOD.

Especially advantageous has proven to be the use of isopropyl esters of $C_{12}$-$C_{18}$-carboxylic acids, in particular the use of isopropyl myristate, and particularly preferably mixtures of isopropyl myristate with $C_{10}$-$C_{13}$-isoparaffin mixtures, the latter preferably having a vapor pressure at 20° C. of from about 10-about 400 Pa.

Another particularly preferred ester oil is triethyl citrate. Further preferred products as contemplated herein contain triethyl citrate and at least one $C_8$-$C_{16}$ isoparaffin selected from isononane, isodecane, isoundecane, isododecane, isotridecane, isotetradecane, isopentadecane and isohexadecane, and mixtures of these isoparaffins. Further preferred products as contemplated herein contain triethyl citrate and at least one $C_8$-$C_{16}$ isoparaffin selected from isononane, isodecane, isoundecane, isododecane, isotridecane and mixtures of these $C_8$-$C_{16}$ isoparaffins. Further preferred products as contemplated herein contain triethyl citrate and a mixture of isodecane, isoundecane, isododecane and isotridecane.

The term "triglyceride" as used in the following means "glycerine triester". Further non-volatile oils preferred as contemplated herein are selected from the triglycerides of linear or branched, saturated or unsaturated, optionally hydroxylated $C_{8-30}$ fatty acids, in so far as that these are liquid under standard conditions. Particularly suitable are the use of natural oils, e.g. soybean oil, cottonseed oil, sunflower oil, palm oil, palm kernel oil, linseed oil, almond oil, castor oil, corn oil, rapeseed oil, olive oil, sesame oil, thistle oil, wheat germ oil, peach kernel oil and the liquid fractions of coconut oil and the like. Particular preference is given to synthetic triglyceride oils, in particular capric/caprylic triglycerides, e.g., the commercial products Myritol® 318 or Myritol® 331 (BASF/Cognis) with unbranched fatty acid residues as well as glyceryltriisostearin and glyceryltri (2-ethylhexanoate) with branched fatty acid residues. Such triglyceride oils preferably account for less than about 50% by weight of the total weight of all cosmetic oils in the product as contemplated herein.

Further non-volatile non-silicone oils which are particularly preferred as contemplated herein are selected from the dicarboxylic acid esters of linear or branched $C_2$-$C_{10}$-alkanals, in particular diisopropylpropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Further non-volatile non-silicone oils which are particularly preferred as contemplated herein are selected from the symmetrical, unsymmetrical or cyclic esters of carbonic acid with $C_6$-$C_{20}$ alcohols, e.g., di-n-caprylyl carbonate (Cetiol® CC) or di-(2-ethylhexyl) carbonate (Tegosoft DEC). Esters of carbonic acid with $C_1$-$C_5$-alcohols, e.g., glycerol carbonate or propylene carbonate, are not compounds suitable as cosmetic oil.

Other oils which may be preferred as contemplated herein are selected from the esters of dimers of unsaturated $C_{12}$-$C_{22}$ fatty acids (dimer fatty acids) with monovalent linear, branched or cyclic $C_2$-$C_{18}$ alkanals or with polybasic linear or branched $C_2$-$C_6$ alkanals. The total weight of the dimer fatty acid esters is particularly preferably from 0.5 to 10% by weight, preferably from about 1 to about 5% by weight, based in each case on the weight of the total water-in-oil emulsion, without taking into account the weight of the foaming agent.

Other cosmetic oils which are particularly preferred as contemplated herein are selected from non-volatile silicone oils. Non-volatile silicone oils as contemplated herein are selected from linear polyalkylsiloxanes having a kinematic viscosity at 25° C. of at least about 5 cSt to about 2000 cSt, in particular selected from linear polydimethylsiloxanes having a kinematic viscosity at 25° C. of from about 5 cSt to about 2000 cSt, preferably from about 10 to about 350 cSt, particularly preferably from about 50-about 100 cSt, as are available, e.g., under the trade names Dow Corning® 200 or Xiameter PMX, respectively, from Dow Corning and Xiameter. Further preferred non-volatile silicone oils are phenyltrimethicones having a kinematic viscosity at 25° C. of from about 10 to about 100 cSt, preferably from about 15-about 30 cSt, and cetyl dimethicones.

Preferred agents as contemplated herein contain at least one non-volatile silicone oil, which is preferably selected from linear polyalkylsiloxanes having a kinematic viscosity at 25° C. of from about 5 cSt-about 2000 cSt, preferably from about 10-about 350 cSt, particularly preferably from about 50-about 100 cSt, especially selected from linear polydimethylsiloxanes having a kinematic viscosity at 25° C. of from about 5 cSt-about 2000 cSt, preferably from about 10-about 350 cSt, particularly preferably from about 50-about 100 cSt, in a total amount of from about 0.1-30% by weight, preferably from about 1-about 24% by weight, particularly preferably from about 2-about 18% by weight, extraordinarily preferably from about 4-10% by weight, based in each case on the weight of the total agent.

Of the oils mentioned, some have proven to be particularly suitable since they guarantee the physical and chemical stability of the bleaching agents pastes over long periods of time and are excellently compatible with the other ingredients as contemplated herein. Preferred agents as contemplated herein are exemplified in that they contain from about 22.5 to about 70% by weight, preferably from about 25 to about 65% by weight, more preferably from about 27.5 to about 60% by weight, particularly preferably from about 30 to about 55% by weight, and in particular from about 32.5 to about 50% by weight of oil(s) chosen from the group of paraffin oil, polyisobutene, alkylbenzoates, isopropyl palmitate, $C_{14-22}$-alkanes, isononyl isononanoate.

Particularly preferred agents as contemplated herein contain from about 0.05 to about 40% by weight, preferably from about 0.1 to about 30% by weight, more preferably from about 0.5 to about 25% by weight, particularly preferably from about 1 to about 20% by weight and in particular from about 2.5 to about 15% by weight $C_{14-22}$ alkane(s).

As a further essential ingredient, the preparations as contemplated herein contain from about 1 to about 70% by weight of peroxodisulfate(s) from the group of sodium peroxodisulfate and/or potassium peroxodisulfate and/or ammonium peroxodisulfate.

In this connection, agents which contain certain peroxodisulfates in narrower ranges of amounts have proved to be particularly suitable. Extremely preferred agents contain from about 2.5 to about 65% by weight, preferably from about 5 to about 60% by weight, more preferably from about 7.5 to about 55% by weight, particularly preferably from about 10 to about 50% by weight and in particular from about 12.5 to about 45% by weight of peroxodisulfate(s) from the group of sodium peroxodisulfate and/or potassium peroxydisulfate.

It is highly preferred to always keep the amount of potassium peroxydisulfate significantly greater than the amount of sodium and ammonium peroxydisulfate which may be used. It has been shown that the chemical and physical stability of the agent as contemplated herein increases with increasing potassium peroxydisulfate content in the total amount of peroxodisulfates. In preferred agents, therefore, the weight ratio of potassium peroxydisulfate to sodium and ammonium peroxydisulfate is >about 2, preferably >about 5, more preferably >about 10, even more preferably >about 15 and in particular >about 20. This weight ratio is determined by dividing the percentage by weight of the amount of potassium peroxydisulfate by the sum of the percentage by weight of the amounts of sodium and ammonium peroxydisulfate.

As contemplated herein, the weight ratio of potassium peroxydisulfate contained in the agent to the sodium and ammonium peroxydisulfates contained in the agent is >about 10:1, preferably >about 12.5:1, more preferably >about 15:1, especially preferably about 17.5:1 and in particular >about 20:1.

Extremely preferred agents as contemplated herein comprise from about 0 to about <2.5% by weight, preferably from about 0 to about <1% by weight, more preferably from about 0 to about <0.5% by weight, particularly preferably from about 0 to about <0.1% and in particular 0% by weight of peroxodisulfates chosen from the group of sodium peroxydisulfate and/or ammonium peroxydisulfate.

The agents as contemplated herein may contain at least one natural polymer as a further ingredient. It is possible, for example, to use cellulose derivatives which are used as thickening agents as a natural polymer. Examples are agar agar, carrageenan, alginate, xanthan gum, karaya gum, ghatti gum, tragacanth, scleroglucangum or gum arabic, alginates, pectins, polyoses, guar gums, carob kernel flour, linseed gums, dextrans, pectins, starch fractions and derivatives such as amylose, amylopectin and dextrins, gelatin and casein, as well as cellulose derivatives, for example methylcellulose, carboxyalkylcelluloses such as carboxymethylcellulose and hydroxyalkyl celluloses such as hydroxyethylcellulose.

Natural polymers from the abovementioned classes of substances are commercially available and are sold, for example, under the trade names Deuteron®-XG (anionic heteropolysaccharide based on 6-D-glucose, D-manose, D-glucuronic acid, Schoener GmbH), Deuteron®-XN (nonionic polysaccharide, Schoener GmbH), Protanal RF 6650 alginate (sodium alginate, FMC biopolymer), cekol (cellulose gum, Kelco), Kelzan (xanthan biopolymer, Kelco), xanthanum FN (xanthan biopolymer, Jungbunzlauer), Keltrol, for example, Keltrol CG-T (xanthan biopolymer, Kelco) or Keltrol CG-SFT (xanthan biopolymer, Kelco).

In a preferred embodiment as contemplated herein, the agents as contemplated herein contain xanthan. As contemplated herein, preference is given to those xanthans which result in transparent preparations after soaking. Particular preference is given to the use of the xanthan biopolymer, which is marketed under the trade name Keltrol CG-SFT from Kelco.

In a preferred embodiment, an agent as contemplated herein contains from about 0.1 to about 5% by weight, preferably from about 0.5 to about 4% by weight, more preferably from about 1 to about 3% by weight, particularly preferably from about 1.25 to about 2.5% by weight, and in particular from about 1.5 to about 2% by weight of xanthan.

The agents as contemplated herein can preferably contain fatty alcohols, preferably shorter-chain fatty alcohols having a chain length of 12 to 18 carbon atoms, as a consistency generator. Suitable short-chain fatty alcohols with a saturated $C_{12}$-$C_{18}$ alkyl chain are, for example, dodecyl-1-ol (dodecyl alcohol, lauryl alcohol), tetradecan-1-ol (tetradecyl alcohol, myristyl alcohol), hexadecyl-1-ol (hexadecyl alcohol, cetyl alcohol, palmityl alcohol) and octadecane-1-ol (octadecyl alcohol, stearyl alcohol). A suitable shorter chain fatty alcohol having an unsaturated $C_{12}$-$C_{18}$ alkyl chain is, for example, (9Z)-octadec-9-en-1-ol (oleyl alcohol).

Particularly suitable for physical and chemical stabilization is cetyl stearyl alcohol. In this case, preference is given to agents as contemplated herein which contain from about 1 to about 15% by weight, preferably from about 2 to about 10% by weight, more preferably from about 3.5 to about 8% by weight, particularly preferably from about 4 to about 7% by weight and in particular from about 5 to about 6.5% by weight of cetearyl alcohol.

In addition to the abovementioned fatty alcohols, the agent as contemplated herein may additionally also contain further fatty alcohols which are, for example, from arachyl alcohol (eicosan-1-ol), gadoleyl alcohol (9Z)-icos-9-en-1-ol), arachidonic alcohol ((5Z, 8Z, 11Z, 14Z)-icosa-5,8,11, 14-tetraen-1-ol), heneicosyl alcohol (heneicosan-1-ol), behenyl alcohol (docosan-1-ol), erucyl alcohol (13Z) 13-en-1-ol) and brassidyl alcohol ((13E)-docosen-1-ol).

These long chain fatty alcohols have a chain length of at least 20 carbon atoms. Within this group, special long-chain fatty alcohols have proved to be particularly suitable.

In a particularly preferred embodiment, an agent for bleaching and/or whitening keratin fibers is exemplified in that it contains arachyl alcohol (eicosan-1-ol).

In a further particularly preferred embodiment, an agent for bleaching and/or whitening keratin fibers is exemplified in that it contains behenyl alcohol (docosan-1-ol).

In a further particularly preferred embodiment, an agent for bleaching and/or whitening keratin fibers is exemplified in that it contains arachyl alcohol (eicosan-1-ol) and/or behenyl alcohol (docosan-1-ol).

It has also been found that it is advantageous if the long-chain fatty alcohols, in particular arachyl alcohol (eicosan-1-ol) and/or behenyl alcohol (docosan-1-ol), are contained in the agent as contemplated herein in certain amounts. Preferred agents as contemplated herein contain one or more long-chain fatty alcohols (a) chosen from the group of arachyl alcohol (eicosan-1-ol), gadoleyl alcohol (9Z)-icos-9-en-1-ol), arachidone alcohol (5Z, 8Z, 11Z, 14Z)-icosa-5,8,11,14-tetraen-1-ol), heneicosyl alcohol (heneicosan-1-ol), behenyl alcohol (docosan-1-ol), erucyl alcohol ((13Z)-docos-13-en-1-ol) and brassidyl alcohol ((13E)-docosen-1-ol) in a total amount of from about 0.3 to about 3.4% by weight, preferably from about 0.4 to about 2.6% by weight, more preferably of from about 0.5 to about 1.8% by weight and particularly preferably from about 0.6 to about 0.9% by weight, based on the total weight of the application-preparing agent.

In a very particularly preferred embodiment, an agent as contemplated herein is exemplified in that it contains as fatty alcohol(s) arachyl alcohol (eicosan-1-ol) and/or behenyl alcohol (docosan-1-ol) in a total quantity of from about 0.3 to about 3.4% by weight, preferably from about 0.4 to about 2.6% by weight, more preferably from about 0.5 to about 1.8% by weight and particularly preferably from about 0.6 to about 0.9% by weight, based on the total weight of the application-preparing agent.

Furthermore, the bleaching agents may contain alkalizing agents. Preferred alkalizing agents are, for example, ammonia, alkanolamines, basic amino acids, as well as inorganic alkalizing agents such as (earth) alkali metal hydroxides, (earth) alkali metal metasilicates, (earth) alkali metal phosphates and (earth) alkali metal hydrogen phosphates. Preferred metal ions are lithium, sodium and/or potassium.

Inorganic alkalizing agents which can be used as contemplated herein are preferably selected from sodium hydroxide, potassium hydroxide, calcium hydroxide, barium hydroxide, sodium phosphate, potassium phosphate, sodium silicate, potassium silicate, magnesium silicate, sodium carbonate and potassium carbonate. Particular preference is given to sodium hydroxide and/or potassium hydroxide.

Alkalizing agents which can be used as contemplated herein are preferably selected from alkanolamines from primary, secondary or tertiary amines with a $C_2$-$C_6$ alkyl basic body which carries at least one hydroxyl group. Particularly preferred alkanolamines are selected from the group which is formed from 2-aminoethan-1-ol (monoethanolamine), 3-aminopropan-1-ol, 4-aminobutan-1-ol, 5-aminopentan-1-ol, 1-aminopentan-2-ol, (monoisopropanolamine), 1-aminobutane-2-01, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methylpropan-2-ol, 3-amino-propane-1,2-diol, 2-amino-2-methyl-2-methylpropane-1,3-diol, 2-amino-2-ethyl-1,3-propanediol, N, N-dimethyl ethanolamine, methylglucamine, triethanolamine, diethanolamine and triisopropanolamine. Particularly preferred alkanolamines are monoethanolamine, 2-amino-2-methylpropanol and triethanolamine.

The basic amino acids which can be used as the alkalinizing agents as contemplated herein are preferably selected from the group that is formed from L-arginine, D-arginine, D/L-arginine, L-lysine, D-lysine, D/L-lysine, L-ornithine, D-ornithine, D/L-ornithine, L-histidine, D-histidine and/or D/L-histidine. Particular preference is given to using L-arginine, D-arginine and/or D/L-arginine as an alkalizing agent in the context of the present disclosure.

Some customers feel that the intense odor of ammonia is annoying or disturbing. Although ammonia is a preferred alkalizing agent, ready-to-use preparations which are free from ammonia can therefore be preferred as contemplated herein. Preferred alkalizing agents for preparations which are free from ammonia are silicates or monoethanolamine, 2-amino-2-methylpropanol and triethanolamine.

Particularly preferred agents as contemplated herein are exemplified in that they contain from about 0 to <about 0.1% by weight, preferably from about 0 to <about 0.05% by weight, more preferably from about 0 to <about 0.01% by weight, particularly preferably from about 0 to <about 0.001% by weight and in particular 0% by weight of ammonia.

If the ready-to-use mixtures contain alkalizing agents, preparations as contemplated herein are preferred which contain alkalinizing agents in an amount from about 0.05 to about 20% by weight, in particular from about 0.5 to about 10% by weight, based in each case on the total weight of the application-preparing agent.

The compositions as contemplated herein may additionally contain at least one further bleaching booster which is different from the inorganic persalts.

Compounds which, under perhydrolysis conditions, yield aliphatic peroxocarboxylic acids having preferably 1 to 10 carbon atoms, in particular 2 to 4 carbon atoms, and/or possibly substituted perbenzoic acid, can be used as bleaching promoters. Substances which carry 0- and/or N-acyl groups of the abovementioned C-atom number and/or optionally substituted benzoyl groups are suitable. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycoluriles, in particular tetraacetylglycoluril (TAGU), N-acylimides, in particular N-nonanoylsuccinimide (NOSI), acylated phenolsulfonates, in particular n-nonanoyl- or isononanoyloxybenzene-sulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran.

The compositions as contemplated herein are viscid and settling stable shortly after their preparation. Preferably, the amounts of the ingredients are coordinated with one another in such a way that the finished agents have a viscosity suitable for the product category after a short rest period. Particularly preferred agents are exemplified in that they have a viscosity 24 h after preparation at 25° C. (Brookfield RV-2, Helipath, Spindle TF, 4 rpm, 60 s) of from about 100 Pas to about 10,000 Pas, preferably from about 150 Pas to about 7,500 Pas, more preferably from about 200 Pas to about 5,000 Pas and in particular of from about 250 Pas to about 2,000 Pas.

A second object of the present disclosure is a method for the color change of keratin fibers in which at least two preparations (A) and (B) packaged separated from each other, of which preparation (A) contains at least one persulphate and preparation (B) contains at least one oxidizing agent, which are mixed into an application mixture, which is applied to the fibers and rinsed again after an exposure time, exemplified in that preparation (A) contains
    a) from about 0.015 to about 10% by weight of ethylene-octene copolymer(s),
    b) from about 5 to about 70% by weight of oil component(s), c) from about 1 to about 70% by weight of peroxodisulfate(s) from the group of sodium peroxodisulfate and/or potassium peroxodisulfate, d) ≤about 0.1% by weight of free water.

The ready-to-use agents are prepared immediately before application to the hair by mixing the two preparations (A) and (B) and optionally a third preparation (C) and/or further preparations. In the case of ready-to-use agents which are mixed from more than two preparations to form a final application mixture, it may be immaterial whether two preparations are first mixed with one another and then the third preparation is added and mixed, or all preparations are combined together and subsequently mixed. The mixing can be performed by stirring in a dish or a cup or by shaking in a closable container.

The term "immediate" is to be understood as a period of a few seconds to one hour, preferably to 30 minutes, in particular to 15 minutes.

The agents as contemplated herein are used in a method for lightening keratin fibers, in particular human hair, in which the agent is applied to the keratin-containing fibers, left on the fiber at a temperature of room temperature to 45° C. for an exposure time of from about 10 to about 60 minutes and then rinsed out with water or washed out with a shampoo.

The application time of the ready-for-use lightening agents is preferably from about 10 to about 60 minutes, in particular from about 15 to about 50 minutes, particularly preferably from about 20 to about 45 minutes. During the exposure time of the agent to the fiber, it may be advantageous to assist the lightening process by supplying heat. The heat supply can be effected by employing an external heat source, such as with the aid of a warm air blower, as well as, particularly in the case of hair lightening in the living subject, by the body temperature of the subject. In the case of the latter possibility, the part to be lightened is usually covered with a hood. An exposure phase at room temperature is also as contemplated herein. The temperature is preferably between about 20° C. and about 40° C., in particular between about 25° C. and about 38° C., during the exposure time. The lightening agents already result in good bleaching and lightening results even at physiologically tolerable temperatures of below about 45° C.

After the end of the exposure time, the remaining lightening preparation is rinsed with water or a cleansing agent from the hair. The cleaning agent can in this connection be, in particular, commercial shampoo, wherein in particular, the cleaning agent can be dispensed with, and the rinsing process can be carried out with tap water if the lightening agent has a carrier containing strong surfactants.

The preferred embodiments of the first object of the present disclosure also apply, necessary changes having been made, to the second object of the present disclosure.

With respect to the viscosity of the application mixture from the agent as contemplated herein and the developer emulsion or other components, methods as contemplated herein are preferred in which the application mixture 24 h after the production at 25° C. has a viscosity (Brookfield RV-2, Helipath, spindle TF, 4 rpm, 60 s) from about 1 Pas to about 100 Pas (from about 103 mPas to about 105 mPas), preferably from about 5 Pas to about 80 Pas (from about 5×103 mPas to about 8×104 mPas), more preferably from about 10 Pas to about 65 Pas (from about 104 mPas to about 6.5×104 mPas) and in particular from about 10 Pas to about 50 Pas (from about 104 mPas to about 5×104 mPas).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for lightening keratin fibers, comprising—based on its weight
   a) from about 0.015 to about 10% by weight of ethylene-octene copolymer(s),
   b) from about 5 to about 70% by weight of oil component(s),
   c) from about 1 to about 70% by weight of peroxodisulfate(s) chosen from the group of sodium peroxodisulfate and/or potassium peroxodisulfate and/or ammonium peroxodisulfate,
   d) ≤about 1% by weight free water, and
   e) about 0.3 to about 3.4% by weight arachyl alcohol, behenyl alcohol, or a combination thereof.

2. The agent according to claim 1, comprising from about 0.05 to about 7.5% by weight of ethylene-octene copolymer(s).

3. The agent according to claim 1, comprising block copolymers of ethylene and octene which contain structural units of the formulas (I) and (II):

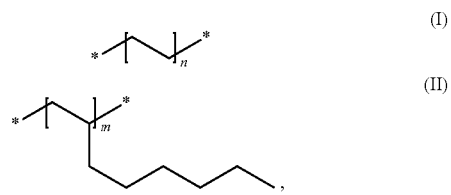

in which n and m, independently of one another, are integers from 10 to about 500.

4. The agent according to claim 1, comprising from about 5 to about 40% by weight of oil(s) chosen from $C_{14-22}$-alkanes.

5. The agent according to claim 1, comprising from about 22.5 to about 70% by weight of oil(s) chosen from the group of paraffin oil, polyisobutene, the alkylbenzoates, isopropyl palmitate, the $C_{14-22}$-alkanes, isononyl isononanoate, and combinations thereof.

6. The agent according to claim 1, comprising from about 2.5 to about 65% by weight of peroxodisulfate(s) chosen from the group of sodium peroxodisulfate and/or potassium peroxydisulfate.

7. The agent according to claim 1, comprising from about 0 to < about 0.1% by weight of ammonia.

8. The agent according to claim 1, having 24 hours after production at 25° C. a viscosity (Brookfield RV-2, Helipath, spindle TF, 4 rpm, 60 s) of from about 100 Pas to about 10,000 Pas.

9. A method for the color change of keratin fibers in which at least two preparations (A) and (B) packaged separately from each other, of which preparation (A) comprises at least one persulphate and preparation (B) comprises at least one oxidizing agent, are mixed to form an application mixture, wherein the application mixture is applied to the fibers and is rinsed off again after an exposure time, and wherein preparation (A) comprises a) from about 0.015 to about 10% by weight of ethylene-octene copolymer(s),
 b) from about 5 to about 70% by weight of oil component(s),
 c) from about 1 to about 70% by weight of peroxodisulfate(s) chosen from the group of sodium peroxodisulfate and/or potassium peroxodisulfate,
 d) ≤about 1% by weight of free water, and
 e) about 0.3 to about 3.4% by weight arachyl alcohol, behenyl alcohol, or a combination thereof.

10. The method according to claim 9, wherein the application mixture at 25° C. has a viscosity (Brookfield RV-2, Helipath, spindle TF, 4 rpm, 60 s) of from about 1 Pas to about 100 Pas.

11. The agent according to claim 1, comprising from about 0.4 to about 3% by weight of ethylene-octene copolymer(s).

12. The agent according to claim 1, comprising from about 5 to about 15% by weight of oil(s) chosen from $C_{14\text{-}22}$-alkanes.

13. The agent according to claim 1, comprising from about 32.5 to about 50% by weight, of oil(s) chosen from the group of paraffin oil, polyisobutene, the alkylbenzoates, isopropyl palmitate, the $C_{14\text{-}22}$-alkanes, isononyl isononanoate, or combinations thereof.

14. The agent according to claim 1, comprising from about 12.5 to about 45% by weight of peroxodisulfate(s) chosen from the group of sodium peroxodisulfate and/or potassium peroxydisulfate.

15. The agent according to claim 1, comprising 0% by weight of ammonia.

16. The agent according to claim 1, having 24 hours after production at 25° C. a viscosity (Brookfield RV-2, Helipath, spindle TF, 4 rpm, 60 s) of from about 250 Pas to about 2,000 Pas.

17. The method according to claim 9, wherein the application mixture at 25° C. has a viscosity (Brookfield RV-2, Helipath, spindle TF, 4 rpm, 60 s) of from about 10 Pas to about 50 Pas.

18. An agent for lightening keratin fibers, comprising—based on its weight, a) from about 0.4 to about 3% by weight of ethylene-octene copolymer(s),
 b) from about 32.5 to about 50% by weight, of oil(s) chosen from the group of paraffin oil, polyisobutene, the alkylbenzoates, isopropyl palmitate, the $C_{14\text{-}22}$-alkanes, isononyl isononanoate, or combinations thereof,
 c) from about 12.5 to about 45% by weight of peroxodisulfate(s) chosen from the group of sodium peroxodisulfate and/or potassium peroxydisulfate,
 d) ≤about 1% by weight free water, and
 e) about 0.6 to about 0.9% by weight arachyl alcohol, behenyl alcohol, or a combination thereof.

19. The agent according to claim 18, comprising 0% by weight of ammonia.

\* \* \* \* \*